United States Patent
Brennan et al.

(10) Patent No.: US 9,594,259 B2
(45) Date of Patent: *Mar. 14, 2017

(54) MASK LENS DESIGN AND METHOD FOR PREVENTING AND/OR SLOWING MYOPIA PROGRESSION

(71) Applicant: Johnson & Johnson Vision Care, Inc., Jacksonville, FL (US)

(72) Inventors: Noel A. Brennan, Ponte Vedra Beach, FL (US); Khaled A. Chehab, Jacksonville, FL (US); Xu Cheng, St. Johns, FL (US); Kurt John Moody, Jacksonville, FL (US); Jeffrey H. Roffman, Saint Johns, FL (US); Xin Wei, Arlington, TX (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 162 days.

This patent is subject to a terminal disclaimer.

(21) Appl. No.: 14/472,623

(22) Filed: Aug. 29, 2014

(65) Prior Publication Data

US 2016/0062145 A1    Mar. 3, 2016

(51) Int. Cl.
| | |
|---|---|
| *A61F 2/16* | (2006.01) |
| *G02C 7/06* | (2006.01) |
| *G02C 7/04* | (2006.01) |
| *A61F 2/14* | (2006.01) |
| *G02C 7/16* | (2006.01) |

(52) U.S. Cl.
CPC ............. *G02C 7/06* (2013.01); *A61F 2/145* (2013.01); *A61F 2/16* (2013.01); *G02C 7/041* (2013.01); *G02C 7/044* (2013.01); *A61F 2/1618* (2013.01); *A61F 2/1659* (2013.01);
(Continued)

(58) Field of Classification Search
CPC .......... A61F 2/142; A61F 2/145; A61F 2/147; A61F 2/16; A61L 27/16; G02C 7/046; G02C 7/16–7/165
See application file for complete search history.

(56) References Cited

U.S. PATENT DOCUMENTS

| | | |
|---|---|---|
| 5,786,883 A | 7/1998 | Miller |
| 6,045,578 A | 4/2000 | Collins et al. |
| 2011/0040376 A1* | 2/2011 | Christie ............... A61F 2/1613 623/6.17 |

FOREIGN PATENT DOCUMENTS

EP    1967892 A1    9/2008

OTHER PUBLICATIONS

Fritsch, F., et al., "Monotone Piecewise Cubic Interpolation", SIAM, J. Numerical Analysis, vol. 17, pp. 238-246 (1980).
(Continued)

*Primary Examiner* — David H Willse
*Assistant Examiner* — Tiffany Shipmon
(74) *Attorney, Agent, or Firm* — Carl J. Evens

(57) ABSTRACT

Contact lenses incorporate mask lens designs that at least one of slow, retard or preventing myopia progression. The lens includes a first zone at a center of the lens; at least one peripheral zone surrounding the center and having a dioptric power that is different than that at the center; and an opaque mask beginning at a radial distance from the center, thereby providing a lens power profile having substantially equivalent foveal vision correction to a single vision lens, and having a depth of focus and reduced retinal image quality sensitivity that slows, retards, or prevents myopia progression.

13 Claims, 9 Drawing Sheets

(52) U.S. Cl.
CPC ...... *A61F 2002/1696* (2015.04); *G02C 7/048* (2013.01); *G02C 7/165* (2013.01); *G02C 2202/24* (2013.01)

(56) References Cited

OTHER PUBLICATIONS

Thibos, L, et al, "Accuracy and Precision of Objective Refraction From Wavefront Aberrations", Journal of Vision, vol. 4, pp. 329-351 (2004).
European Search Report for corresponding European Patent Appln. No. 15182990.0 dated Dec. 16, 2015.

\* cited by examiner

Through Focus Curve - Calculated DoF: 1.22D

Through Focus Curve - Calculated DoF: 1.17D

MASK LENS DESIGN AND METHOD FOR PREVENTING AND/OR SLOWING MYOPIA PROGRESSION

BACKGROUND OF THE INVENTION

Field of the Invention

The present invention relates to ophthalmic lenses, and more particularly, to contact lenses designed to slow, retard, or prevent myopia progression. The ophthalmic lenses of the present invention comprise mask lens designs that provide improved foveal vision correction, increased depth of focus (DOF), and an optimized retinal image at a range of accommodative distances that makes the degradation of retinal image quality less sensitive to blur during near work activities, thereby preventing and/or slowing myopia progression.

Discussion of the Related Art

Common conditions which lead to reduced visual acuity include myopia and hyperopia, for which corrective lenses in the form of spectacles, or rigid or soft contact lenses, are prescribed. The conditions are generally described as the imbalance between the length of the eye and the focus of the optical elements of the eye. Myopic eyes focus in front of the retinal plane and hyperopic eyes focus behind the retinal plane. Myopia typically develops because the axial length of the eye grows to be longer than the focal length of the optical components of the eye, that is, the eye grows too long. Hyperopia typically develops because the axial length of the eye is too short compared with the focal length of the optical components of the eye, that is, the eye does not grow long enough.

Myopia has a high prevalence rate in many regions of the world. Of greatest concern with this condition is its possible progression to high myopia, for example greater than five (5) or six (6) diopters, which dramatically affects one's ability to function without optical aids. High myopia is also associated with an increased risk of retinal disease, cataracts, and glaucoma.

Corrective lenses are used to alter the gross focus of the eye to render a clearer image at the retinal plane, by shifting the focus from in front of the plane to correct myopia, or from behind the plane to correct hyperopia, respectively. However, the corrective approach to the conditions does not address the cause of the condition, but is merely prosthetic or intended to address symptoms. More importantly, correcting the myopic defocus of the eye does not slow or retard myopia progression.

Most eyes do not have simple myopia or hyperopia, but have myopic astigmatism or hyperopic astigmatism. Astigmatic errors of focus cause the image of a point source of light to form as two mutually perpendicular lines at different focal distances. In the following discussion, the terms myopia and hyperopia are used to include simple myopia or myopic astigmatism and hyperopia and hyperopic astigmatism respectively.

Emmetropia describes the state of clear vision where an object at infinity is in relatively sharp focus with the crystalline lens relaxed. In normal or emmetropic adult eyes, light from both distant and close objects and passing though the central or paraxial region of the aperture or pupil is focused by the crystalline lens inside the eye close to the retinal plane where the inverted image is sensed. It is observed, however, that most normal eyes exhibit a positive longitudinal spherical aberration, generally in the region of about +0.50 Diopters (D) for a 5.0 mm aperture, meaning that rays passing through the aperture or pupil at its periphery are focused +0.50 D in front of the retinal plane when the eye is focused to infinity. As used herein the measure D is the dioptric power, defined as the reciprocal of the focal distance of a lens or optical system, in meters.

The spherical aberration of the normal eye is not constant. For example, accommodation (the change in optical power of the eye derived primarily though changes to the crystalline lens) causes the spherical aberration to change from positive to negative.

As noted, myopia typically occurs due to excessive axial growth or elongation of the eye. It is now generally accepted, primarily from animal research, that axial eye growth can be influenced by the quality and focus of the retinal image. Experiments performed on a range of different animal species, utilizing a number of different experimental paradigms, have illustrated that altering retinal image quality can lead to consistent and predictable changes in eye growth.

Furthermore, defocusing the retinal image in both chick and primate animal models, through positive lenses (myopic defocus) or negative lenses (hyperopic defocus), is known to lead to predictable (in terms of both direction and magnitude) changes in eye growth, consistent with the eyes growing to compensate for the imposed defocus. The changes in eye length associated with optical blur have been shown to be modulated by changes in scleral growth. Blur with positive lenses, which leads to myopic blur and a decrease in scleral growth rate, results in the development of hyperopic refractive errors. Blur with negative lenses, which leads to hyperopic blur and an increase in scleral growth rate, results in the development of myopic refractive errors. These eye growth changes in response to retinal image defocus have been demonstrated to be largely mediated through local retinal mechanisms, as eye length changes still occur when the optic nerve is damaged, and imposing defocus on local retinal regions has been shown to result in altered eye growth localized to that specific retinal region.

In humans there is both indirect and direct evidence that supports the notion that retinal image quality can influence eye growth. A variety of different ocular conditions, all of which lead to a disruption in form vision, such as ptosis, congenital cataract, corneal opacity, vitreous hemorrhage and other ocular diseases, have been found to be associated with abnormal eye growth in young humans, which suggests that relatively large alterations in retinal image quality do influence eye growth in human subjects. The influence of more subtle retinal image changes on eye growth in humans has also been hypothesized based on optical errors in the human focusing system during near work that may provide a stimulus for eye growth and myopia development in humans.

One of the risk factors for myopia development is near work. Due to accommodative lag or negative spherical aberration associated with accommodation during such near work, the eye may experience hyperopic blur, which stimulates myopia progression as discussed above.

Moreover, the accommodation system is an active adaptive optical system; it constantly reacts to near-objects, as well as optical designs. Even with previously known optical designs placed in front of the eye, when the eye accommodates interactively with the lens+eye system to near objects, continuous hyperopic defocus may still be present leading to myopia progression. Therefore, one way to slow the rate of myopia progression is to design optics that reduces the impact of hyperopic blur on retinal image quality. With such designs, for each diopter of hyperopic defocus the retinal image quality is less degraded. In another sense, the retina is therefore relatively desensitized to hyperopic defocus. In particular, DOF and image quality (IQ) sensitivity may be used to quantify the susceptibility of the eye to myopia progression as a result of hyperopic defocus at the retina. An ophthalmic lens design with larger DOF and low IQ sensitivity will make the degradation of retinal image quality less sensitive to hyperopic defocus, hence slowing down the rate of myopia progression.

In object space, the distance between the nearest and farthest objects of a scene that appear acceptably sharp is called depth of field. In image space, it is called depth of focus (DOF). With a conventional single vision optical design, a lens has a single focal point, with image sharpness decreasing drastically on each side of the focal point. With an optical design with extended DOF, although it may have a single nominal focal point, the decrease in image sharpness is gradual on each side of the focal point, so that within the DOF, the reduced sharpness is imperceptible under normal viewing conditions.

IQ sensitivity can be defined as the slope of retinal IQ-defocus curve at an accommodative demand of 1 to 5 diopters. It indicates how image quality changes with defocus. The larger the value of IQ sensitivity, the more sensitive the image quality is to defocus error during accommodation.

SUMMARY OF THE INVENTION

The mask lens design of the present invention overcomes the limitations of the prior art by ensuring comparable or better distance vision correction with an increased depth of focus and reduced IQ sensitivity, thereby providing myopic treatment.

In accordance with one aspect, the present invention is directed to an ophthalmic lens for at least one of slowing, retarding or preventing myopia progression. An ophthalmic lens comprises a first zone at a center and at least one peripheral zone surrounding the center and having a dioptric power that is different than that at the center. An opaque mask extends from the outermost peripheral zone, thereby providing a power profile having substantially equivalent foveal vision correction to a single vision lens, and having a depth of focus and reduced IQ sensitivity that slows, retards, or prevents myopia progression.

In accordance with another aspect, the present invention is directed to a method for at least one of slowing, retarding or preventing myopia progression. An ophthalmic lens is provided with a power profile having substantially equivalent foveal vision correction to a single vision lens and having a depth of focus and reduced retinal image quality sensitivity that slows, retards, or prevents myopia progression. The power profile comprises a first zone at a center of an ophthalmic lens; at least one peripheral zone surrounding the center and having a dioptric power that is different than at the center; and an opaque mask extending from the at least one peripheral zone. Accordingly, the growth of the eye is altered.

The optical device of the present invention has a mask lens design. As set forth herein, it has been shown that a lens design with larger depth of focus and low image quality sensitivity will make the degradation of retinal image quality less sensitive to hyperopic blur, hence slowing down the rate of myopia progression. Accordingly, the present invention utilizes mask lens designs that provide foveal vision correction, and a depth of focus and also low image quality sensitivity that treats or slows myopia progression.

The mask lens design of the present invention may also be customized to achieve both good foveal vision correction and higher treatment efficacy based on the subject's average pupil size.

The mask lens design of the present invention provides a simple, cost-effective and efficacious means and method for preventing and/or slowing myopia progression.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE INVENTION

Figure 2A:
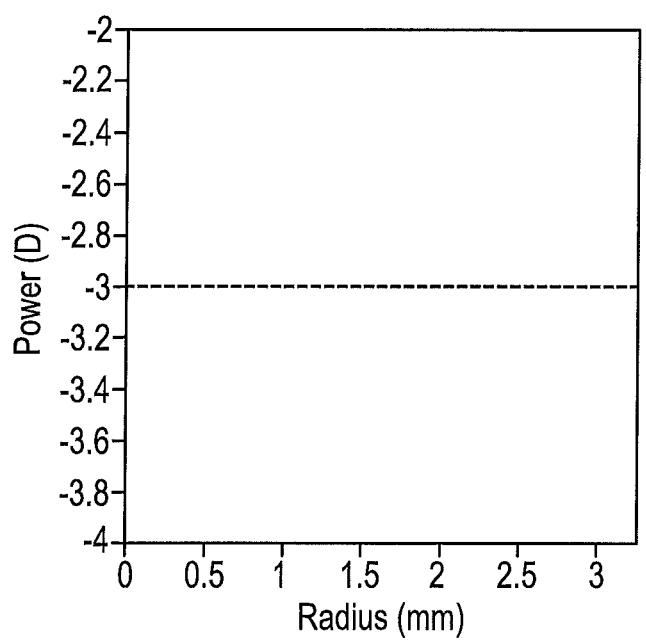
FIGS. 2A, 2B, and 2C are illustrations of power profiles for a spherical lens, an aspheric lens with +1.50 D positive longitudinal spherical aberration (LSA) at a 5.0 mm pupil aperture, and an ACUVUE® bifocal lens (a multiconcentric alternating distance and near zone lens) with +1.50 D add power, respectively.
Figure 2B:
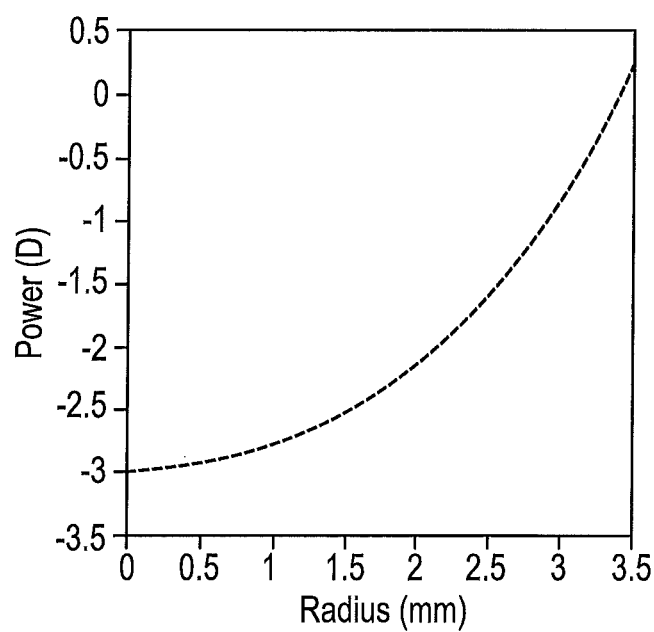
Figure 2C:
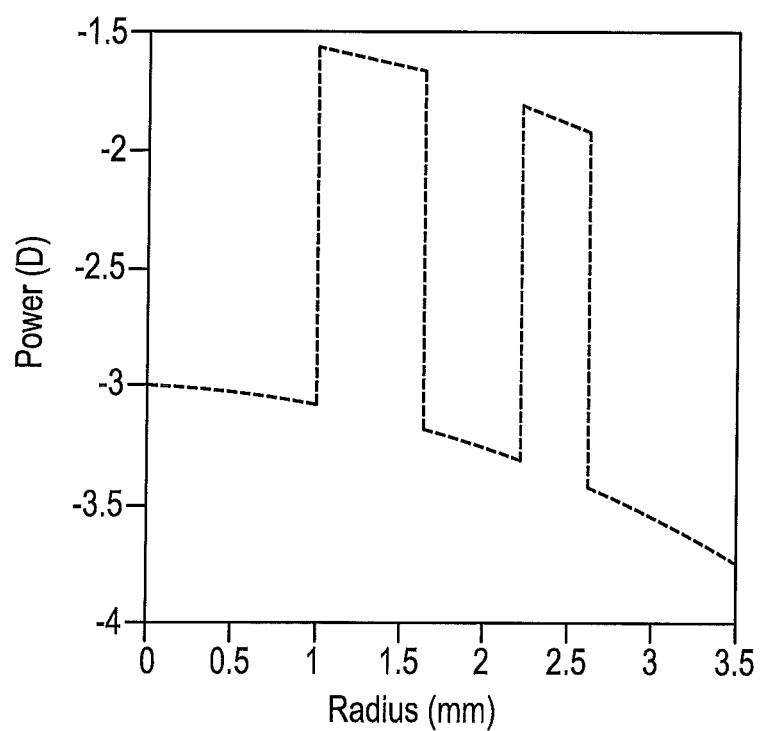

FIGS. 2A, 2B, and 2C are illustrations of power profiles for a spherical lens, an aspheric lens with +1.50 D LSA at 5.0 mm pupil aperture, an ACUVUE® bifocal lens with +1.50 D add power, respectively. There have been observations that the aspheric lens and ACUVUE® bifocal lens both may have an effect on slowing myopia progression. Thus, a mechanism beyond changing spherical aberration, as disclosed in U.S. Pat. No. 6,045,578, is needed for describing lenses for preventing, treating, or slowing myopia progression.

According to the present invention, mask lens designs are developed for ophthalmic lenses that provide foveal vision correction, and have an increased depth of focus and also reduced IQ sensitivity that treats or slows myopia progression.

The mask lens designs according to the present invention may be utilized with ophthalmic lenses having various different power profiles. In accordance with one exemplary embodiment, a mask lens design may be described by:

$$P(r) = P_{Seg}(r) + 24\sqrt{5} \times SA \times \frac{r^2}{3.25^4} - 12\sqrt{5} \times \frac{SA}{3.25^2}, \quad (1)$$
$$r < r_{MASK}$$

wherein P represents the dioptric power (D);
r represents a radial distance from a geometric lens center;
SA represents an amount of spherical aberration; and
$P_{Seg}(r)$ represents a step function that has a number of zones with different magnitudes;

In accordance with another exemplary embodiment, a mask lens design may be described by:

$$P(r) = P_{PCHIP}(r) + 24\sqrt{5} \times SA \times \frac{r^2}{3.25^4} - 12\sqrt{5} \times \frac{SA}{3.25^2}, \quad (2)$$
$$r < r_{MASK}$$

wherein P represents the dioptric power (D);
r represents a radial distance from a geometric lens center;
SA represents an amount of spherical aberration; and
$P_{PCHIP}(r)$ represents a Piecewise Cubic Hermite Interpolating Polynomial curve control by number of points. See Fritsch et al., *Monotone Piecewise Cubic Interpolation*, SIAM J. Numerical Analysis, Vol. 17, 1980, pp. 238-46.

According to the present invention, the mask may comprise a pigmented or tinted opaque region, for example, a colored or black ring. The inner radius of the mask, from a center of the lens, may be from about 2.0 mm to 3.0 mm and may extend to an outer optical zone of the lens, for example, to about 8.0 mm. In specific embodiments, the mask may have a width of 2.25 mm to 4.5 mm.

To measure vision correction, neural sharpness at 4.5 mm EP (entrance pupil) and 6.5 mm EP is utilized as a determinant of retinal image quality. It is important to note that any other suitable means and/or methods (for example, area under the MTF curve, Strehl ratio, and the like) that measure the goodness of retinal image quality may be utilized.

Neural sharpness is given by the following equation:

$$NS = \frac{\int_{-\infty}^{\infty}\int_{-\infty}^{\infty} psf(x,y) g_N(x,y) dx dy}{\int_{-\infty}^{\infty}\int_{-\infty}^{\infty} psf_{DL}(x,y) g_N(x,y) dx dy}, \quad (3)$$

wherein psf or point-spread function is the image of a point object and is calculated as the squared magnitude of the inverse Fourier transform of the pupil function P(X,Y) where P(X,Y) is given by $$P(X,Y) = A(X,Y) \exp(ik\, W(X,Y)), \quad (4)$$

wherein k is the wave number (2π/wavelength) and A(X,Y) is an optical apodization function of pupil coordinates X,Y, $psf_{DL}$ is the diffraction-limited psf for the same pupil diameter, and $g_N$ (X,Y) is a bivariate-Gaussian, neural weighting function. For a more complete definition and calculation of neural sharpness see Thibos et al., *Accuracy and precision of objective refraction from wave front aberrations*, Journal of Vision (2004) 4, 329-351, which discusses the problem of determining the best correction of an eye utilizing wave front aberrations. The wave front W(X,Y) of the contact lens and the eye is the sum of each as given by:

$$W_{CL+eye}(X,Y) = W_{CL}(X,Y) + W_{eye}(X,Y). \quad (5)$$

To determine image quality (IQ) sensitivity or slope of a lens+eye system for an object at a specific target vergence, three major steps are required: identification of coupling effect of ocular accommodation system, estimation of the corresponding accommodating state for the object, and calculation of the image quality sensitivity:

Step 1: Identification of coupling effect of ocular accommodation system: As the human eye accommodates from distance to near, two ocular structures change simultaneously: the iris aperture becomes smaller; the crystal lens becomes bulkier. These anatomical changes leads to three optical related parameters change in a coupled manner in the lens+eye system: entrance pupil diameter, defocus (e.g. Zernike defocus $Z_2^0$), and spherical aberration (e.g. Zernike spherical aberration $Z_4^0$). Note in particular, since the pupil size decreases as the target moves closer and conventional Zernike defocus and spherical aberration highly depends on the pupil sizes, it is challenging to specify the these Zernike aberration terms in a conventional manner. As an alternative, to gauge the Zernike defocus and aberration across different pupil sizes, these terms were sometimes presented in a 'diopter' manner. To convert to the classic Zernike coefficients via equations as follows:

$$Z_{20}^{microns} = Z_{20}^{Diopter} * (EPD/2)^2 / (4*\sqrt{3})$$

$$Z_{40}^{microns} = Z_{40}^{Diopter} * (EPD/2)^4 / (24*\sqrt{5})$$

wherein EPD is the diameter the entrance pupil, $Z_{20}^{Diopter}$ (unit: D) and $Z_{40}^{Diopter}$ (unit: D/mm²), note sometimes in the figures, as well as in some literatures, the unit of this term is also specified as 'D' in short) are the Zernike defocus and spherical aberration terms specified in 'diopter' manner, and $Z_{20}^{microns}$ and $Z_{40}^{microns}$ are corresponding conventional Zernike terms.

Figure 1A:
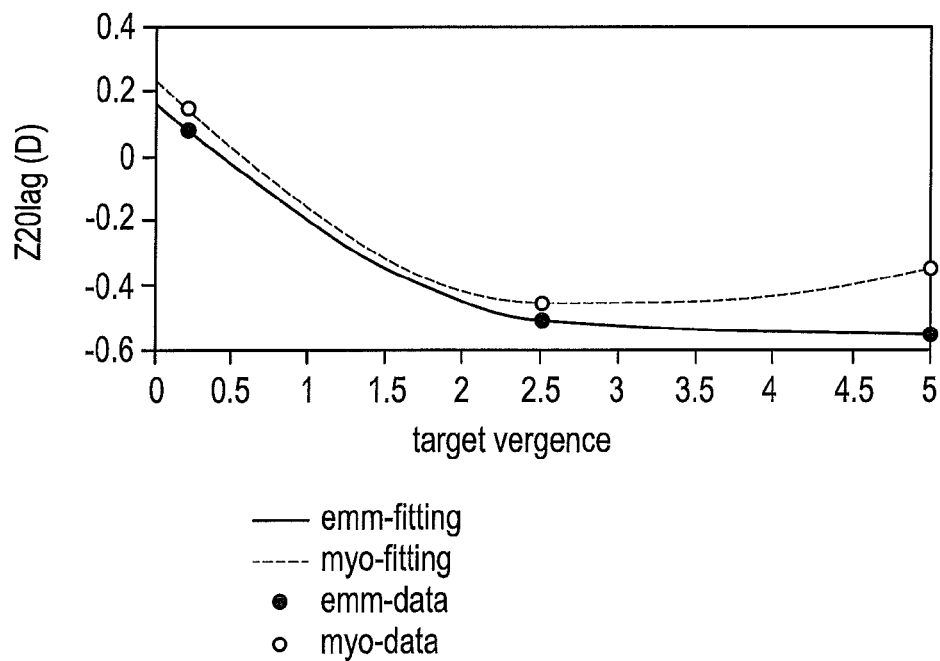
FIGS. 1A, 1B and 1C. Illustrate the change of Defocus $Z^0_2$, Spherical aberration $Z^0_4$ terms, and entrance pupil diameter as a function of vergance for myopic and emmetropic population.
Figure 1B:
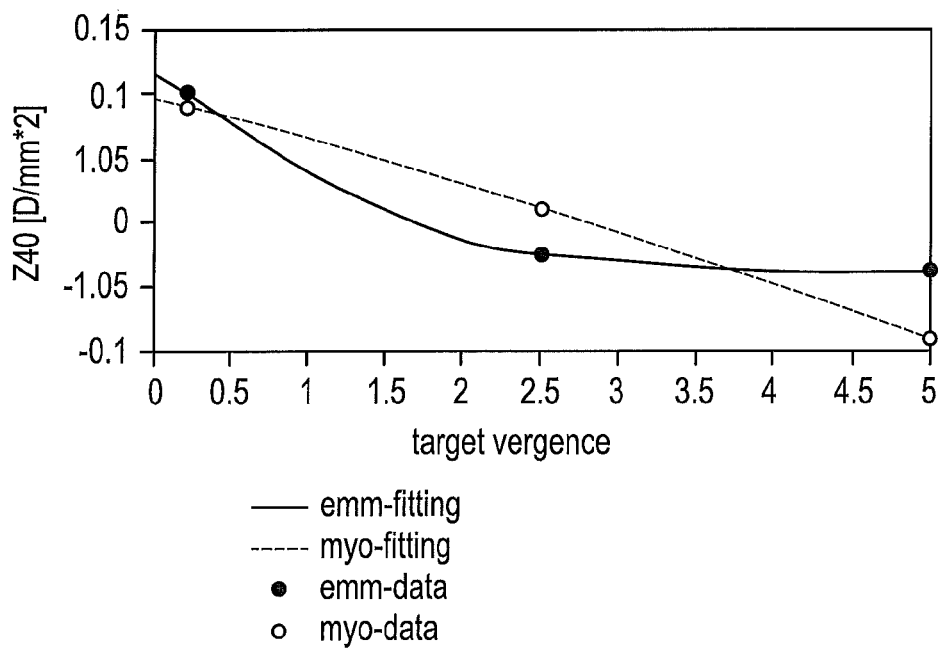
Figure 1C:
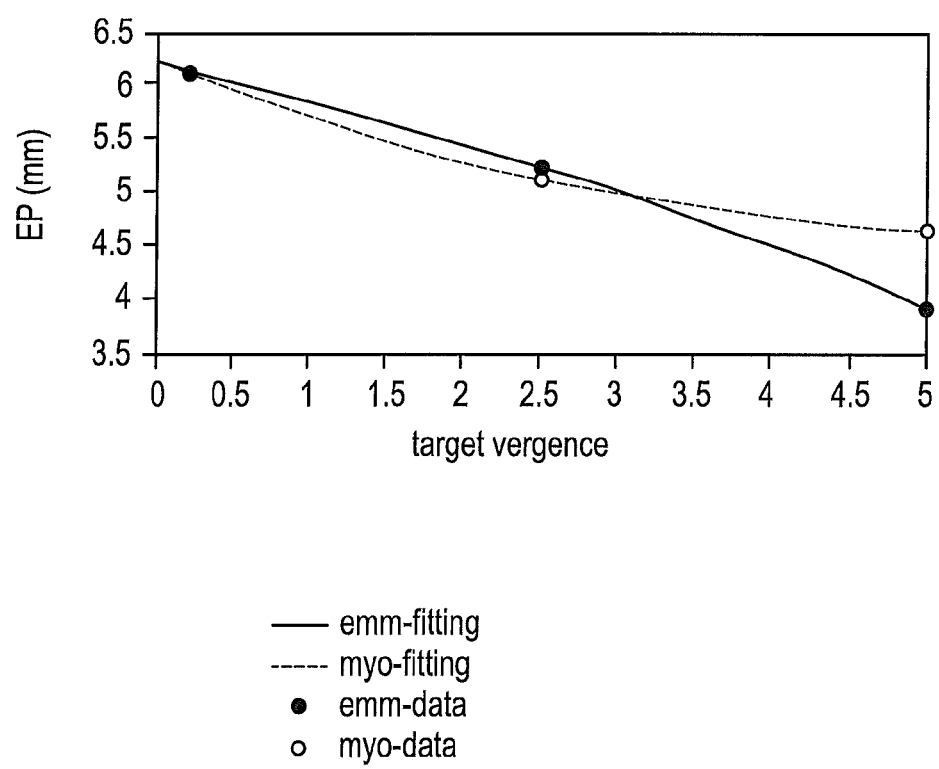

Ghosh et al 2012 (Axial Length Changes with Shifts of Gaze Direction in Myopes and Emmetropes, IOVS, September 2012, VOL. 53, No. 10) measured the change of these three parameters in relation to target vergence for emmetropes and myopes. FIG. 1A, is a graphical representation of defocus vs. target vergence, FIG. 1B, is graphical representation of Spherical Aberration vs. Target Vergence and FIG. 1C, is a graphical representation of enterance pupil diameter vs. target vergence. As the target vergence changes, these three parameters change simultaneously. Since these data were measured on the human subject eyes without contact lens, the relation between these optical parameters and target vergence with lens+eye system differs. Nevertheless the coupling relation among the optical parameters (entrance pupil size, defocus, and spherical aberration) remains the same because their changes originate from the same anatomical source. Different interpolation techniques could then be used to model such coupling relations among the three parameters from the experimental data.

Step 2: Estimation of the Corresponding Accommodating State for the Object at Near:

Once the coupling relation among the entrance pupil, defocus and spherical aberration during the accommodation is modeled at step 1, it could then be used to estimate the resting accommodating state of lens+eye system for a target at any given distance. The scientific essence of this step is to find how the eye accommodates to the near target in the presence of contact lens. For example, a target at specific distance at near (e.g. 2 D) results blurs for a distance corrected lens+eye system (e.g. the system that combines the lens in FIG. 3A and an eye model 0.06 D/mm$^2$ SA). To determine the resting accommodating state of this system, the entrance pupil, defocus, and spherical aberration of the eye were systematically adjusted per the coupling model in step 1 so that the corresponding image quality improves to a threshold. For example in FIG. 3C, the entrance pupil, defocus, and spherical aberration are found to be 4.5 mm, 1.3 D, 0.04 D/mm$^2$ to boost the image quality (NS) to be −1.6 (roughly 20/25 VA).

Calculation of the image quality sensitivity for the specific target vergence: Once the accommodating state, and the corresponding entrance pupil, defocus, and spherical aberration are determined, the retina image quality sensitivity or slope could be readily calculated as follows:

$$\text{IQ sensitivity} = d \cdot NS/d \cdot Rx, \quad (6)$$

wherein d·NS/d·Rx is the derivative of neural sharpness to defocus value. For example, for design 3A with the standard eye model and target 2 D away, the corresponding IQ sensitivity is calculated to be 0.7.

By setting ranges for the number of zones, width of the zones, magnitudes of the zones, spherical aberration, and radius values in Equation (1), different power profiles can be obtained. Exemplary ranges of these variables are listed below in Table 1.

Figure 3A:
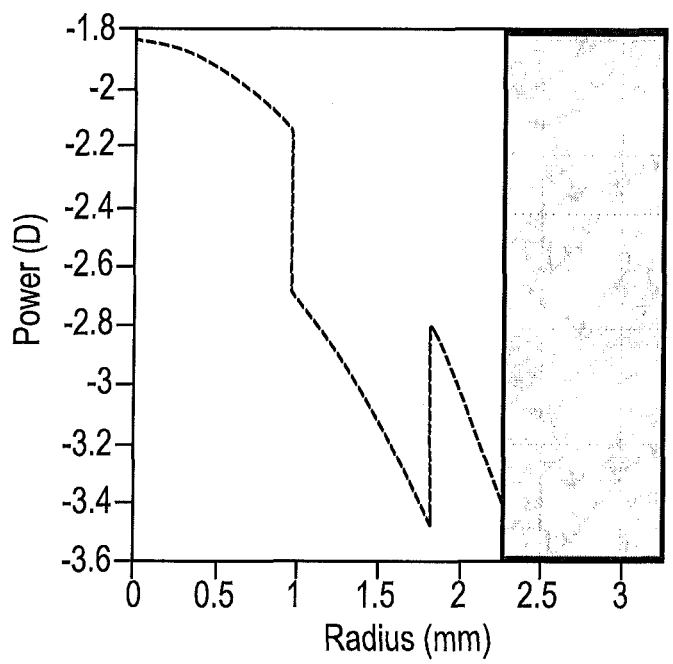
FIG. 3A is an illustration of a power profile for a first mask lens design in accordance with the present invention.
Figure 3B:
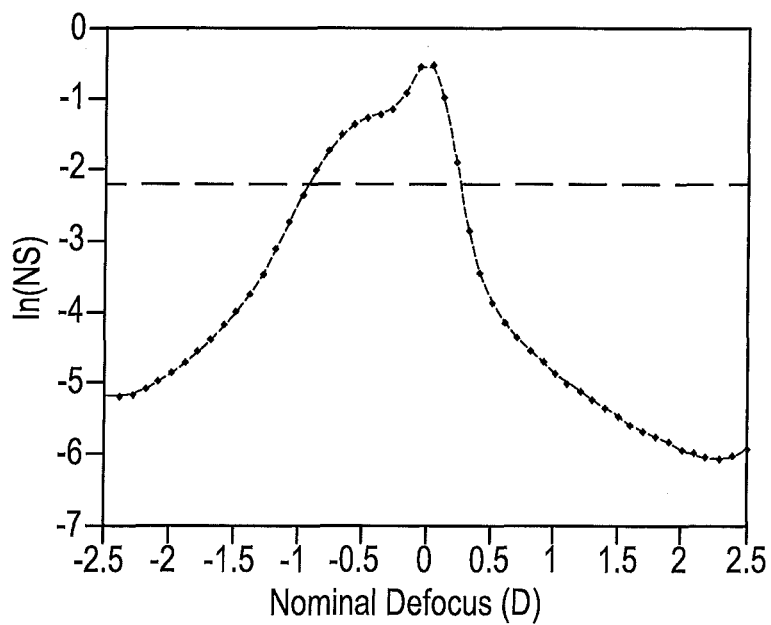
FIG. 3B is a graph showing neural sharpness and depth of focus for the mask lens design of FIG. 3A.

FIG. 3A shows a power profile having a three-zone design, which is stepped or discontinuous, and a mask. In FIG. 3B, image quality (as measured by neural sharpness) would be sharpest at 0.00 diopter defocus, indicating that the optic system carries the sharpest image when it is well focused. As refractive error (both positive and negative) is introduced into the optical system, the image quality starts to drop. A threshold of neural sharpness value is chosen to quantify DOF at −2.2. When the value is larger than −2.2, patients still have reasonably good near vision for reading. In FIG. 3B, a horizontal threshold line at −2.2 is drawn. The line intersects the through-focus curve. The width between the two intersections corresponds to DOF. In this embodiment, the DOF is 1.22 D.

Figure 3C:
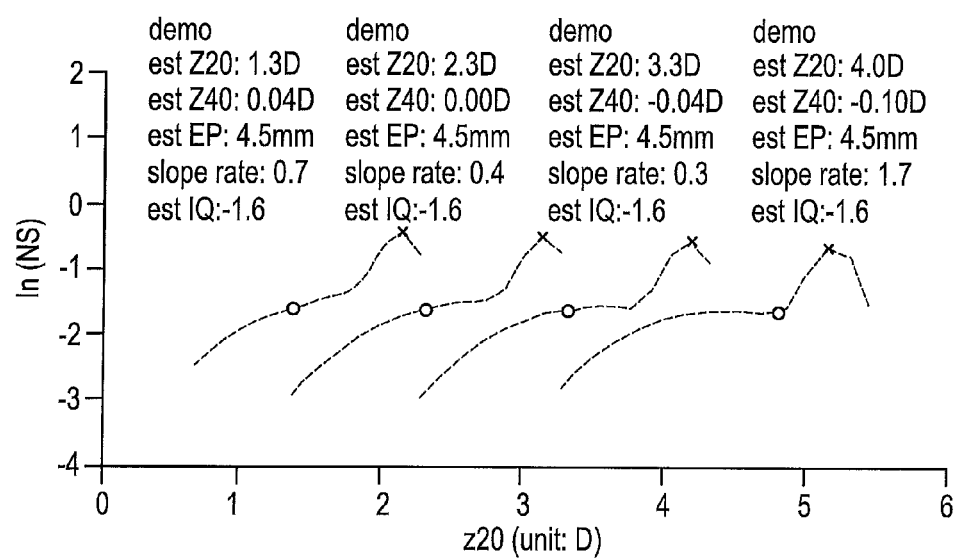
FIG. 3C is a graph showing the neural sharpness at various accommodative states for the mask lens design of FIG. 3A.

With reference to FIG. 3C, a graph is illustrated of neural sharpness at 2 D, 3 D, 4 D and 5 D accommodative states (target vergence) and a calculated defocus error of −0.20 D to −0.70 D, which is typically associated with accommodation lag, for the lens design of FIG. 3A. Each curve is characterized by a shoulder at a threshold value of −1.6, having a specific defocus (Z20), spherical aberration (Z40) and Entrance Pupil size (EP). The slope of the shoulder is indicative of reduced IQ sensitivity. In this embodiment, the IQ sensitivity is 0.66, 0.40, 0.28 and 1.68, respectively.

Based upon the number of points, spherical aberration, height (D input into P$_{PCHIP}$), and radius values entered into Equation (2), different power profiles are obtained. The power profile may be continuous, that is having smooth transitions between different powers in different regions of a lens, that is, there are no abrupt or discontinuous changes between different zones or regions of the lens.

Figure 4A:
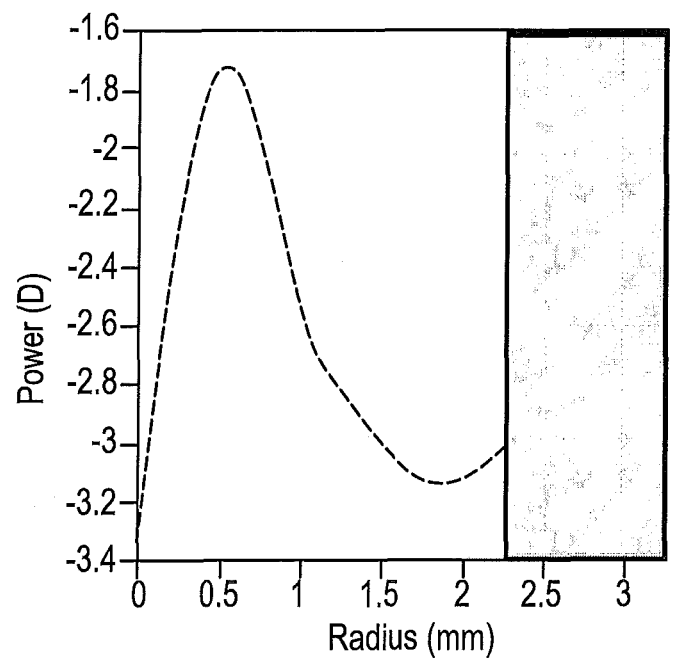
FIG. 4A is an illustration of a power profile for a second mask lens design in accordance with the present invention.

Exemplary values of these variables are listed in Table 3 for a second mask lens design having a power profile as illustrated in FIG. 4A.

TABLE 1

|   | Zone1 Width(mm) | Zone2 Width(mm) | Zone3 Width(mm) | Zone1 mag (D) | Zone2 mag (D) | Zone3 mag (D) | SA (D/mm$^2$) | r$_{mask}$ |
|---|---|---|---|---|---|---|---|---|
| max | 1.0 | 1.0 | 0.5 | 0.5 | 0 | 0.5 | 0 | 3 |
| min | 0.5 | 0.5 | 0 | 0 | −0.5 | 0 | −0.5 | 2 |

A resulting multifocal power profile is illustrated in FIG. 3A. The parameters for a first mask lens design are listed below in Table 2.

TABLE 2

| Design # | Zone1 Width(mm) | Zone2 Width(mm) | Zone3 Width(mm) | Zone1 mag (D) | Zone2 mag (D) | Zone3 mag (D) | SA (D/mm$^2$) | r$_{mask}$ |
|---|---|---|---|---|---|---|---|---|
| #1 FIG. 2A | 0.95 | 0.86 | 0.46 | 0.32 | −0.23 | 0.44 | −0.16 | 2.25 |

TABLE 3

| SA: −0.06 D/mm² $r_{mask}$ = 2.25 mm | | | | | |
|---|---|---|---|---|---|
| | Point # | | | | |
| | 1 | 2 | 3 | 4 | 5 |
| Radial Location (mm) | 0 | 0.56 | 1.13 | 1.69 | 2.25 |
| $P_{PCHIP}$ (D) | −0.67 | 1.00 | 0.11 | −0.07 | 0.28 |

FIG. 4A shows a power profile having a continuous freeform design and a mask. As shown in FIG. 4A, the power in the center of the lens is 0.00 D to 0.50 D more negative than a paraxial power of the lens (−3.00 D). The power then increases progressively from the center to a high point. The magnitude of the high point is 1.00 D to 1.50 D more positive than the paraxial power. The location of the high point A is 0.25 mm to 0.50 mm away from the center. The power drops from a high point to a low point. The power at the low point is 0.00 D to 0.25 D more negative than the paraxial power. After the low point, the power increases at a slower rate to an inner radius of the mask. The magnitude of such increment is less than 0.25 D.

Figure 4B:
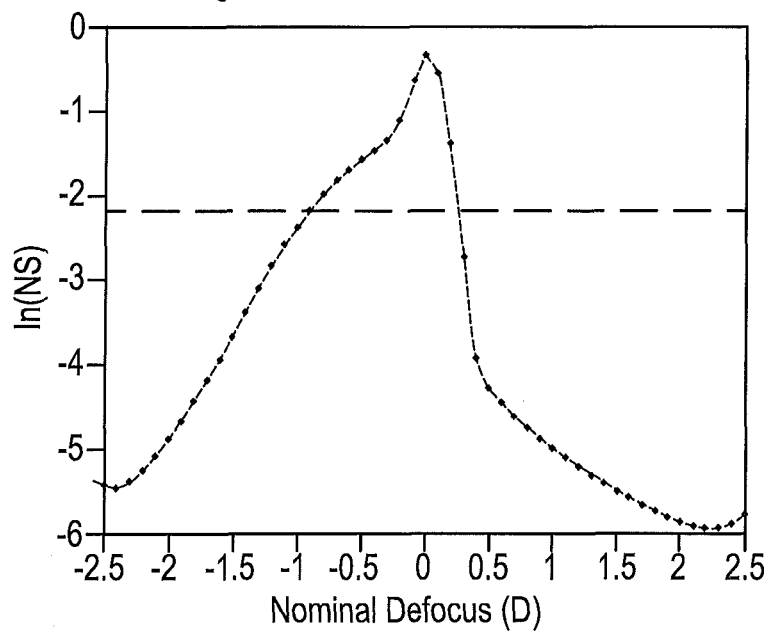
FIG. 4B is a graph showing neural sharpness and depth of focus for the mask lens design of FIG. 4A.

With reference now to FIG. 4B, a horizontal threshold line for neural sharpness is drawn at −2.2. The line intersects the through-focus curve. The width between the two intersections corresponds to DOF. In this embodiment, the DOF is 1.17 D.

Figure 4C:
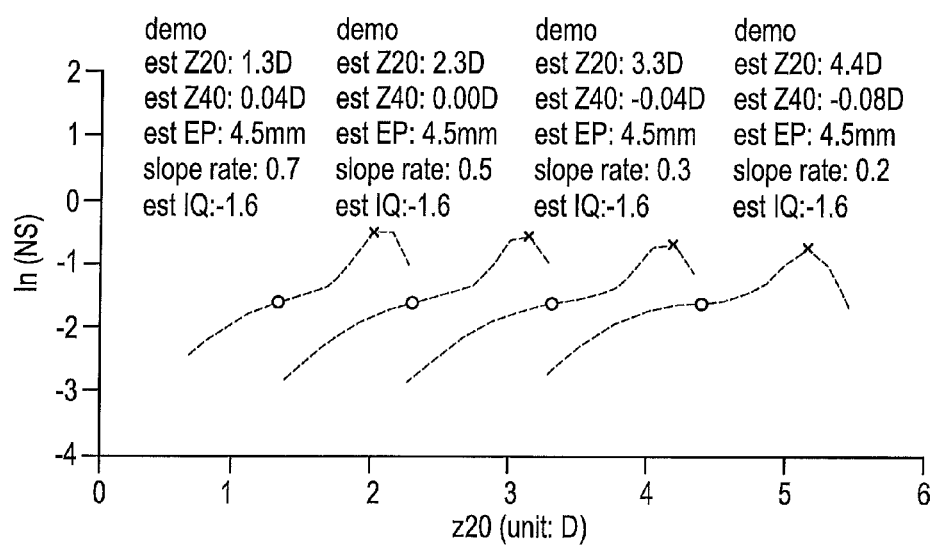
FIG. 4C is a graph showing the neural sharpness at various accommodative states for the mask lens design of FIG. 4A.

With reference to FIG. 4C, a graph is illustrated of neural sharpness at 2 D, 3 D, 4 D and 5 D accommodative states (target vergence) and a calculated defocus error of −0.60 D to −0.70 D, which is typically associated with accommodation lag, for the lens design of FIG. 4A. Each curve is characterized by a shoulder at a threshold value of −1.6, having a specific defocus (Z20), spherical aberration (Z40), and Entrance Pupil size (EP). The slope of the shoulder is indicative of reduced IQ sensitivity. In this embodiment, the IQ sensitivity is 0.70, 0.52, 0.35 and 0.20, respectively.

As shown below in Table 4, neural sharpness at entrance pupil of 4.5 mm and 6.5 mm are calculated for the mask lens designs. The depth of focus (DOF) and IQ sensitivity are calculated at threshold neural sharpness values of −2.2 and −1.6, respectively.

TABLE 4

| | Neural Sharpness 4.5 mm EP | Neural Sharpness 6.5 mm EP | Depth of Focus | IQ Sensitivity at 2D vergence | IQ Sensitivity at 3D vergence | IQ Sensitivity at 4D vergence | IQ Sensitivity at 5D vergence |
|---|---|---|---|---|---|---|---|
| Sphere | −0.4 | −0.54 | 0.76 | 8.15 | 5.98 | 4.43 | 3.75 |
| Aspheric | −0.88 | −1.62 | 1.16 | 1.10 | 1.31 | 3.91 | 5.62 |
| ACUVUE ® bifocal | −1.34 | −2.01 | 0.89 | 2.79 | 2.41 | 0.76 | 0.25 |
| Design #1 FIG. 3A | −0.47 | NA | 1.22 | 0.66 | 0.40 | 0.28 | 1.68 |
| Design #2 FIG. 4A | −0.34 | NA | 1.17 | 0.70 | 0.52 | 0.35 | 0.20 |

As shown in Table 4, the mask lens designs as illustrated in FIGS. 3A and 4A, have better neural sharpness than the aspheric and ACUVUE® bifocal +1.50 add lenses at EP 4.5 mm and comparable depth of focus and a superior myopia treatment efficacy to the aspheric lens as measured by the depth of focus and reduced IQ sensitivity, as illustrated in FIGS. 3C and 4C.

Figure 5:
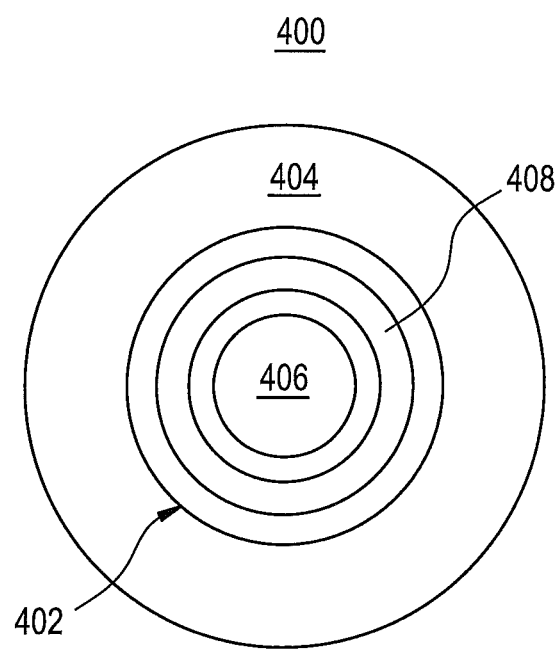
FIG. 5 is a diagrammatic representation of an exemplary contact lens in accordance with the present invention.

Referring to FIG. 5, there is illustrated a diagrammatic view of a contact lens 400 in accordance with the present invention. The contact lens 400 comprises an optic zone 402 and an outer zone 404. The optic zone 402 comprises a first, central zone 406 and at least one peripheral zone 408. In the following examples, the diameter of the optic zone 402 may be selected to be 8 mm, the diameter of the substantially circular first zone 406 may be selected to be 4 mm, and the boundary diameters of an annular outer peripheral zone 408 may be 5.0 mm and 6.5 mm as measured from the geometric center of the lens 400. It is important to note that FIG. 5 only illustrates an exemplary embodiment of the present invention. For example, in this exemplary embodiment, the outer boundary of the at least one peripheral zone 408 does not necessarily coincide with the outer margin of the optic zone 402, whereas in other exemplary embodiments, they may coincide. The outer zone 404 surrounds the optic zone 402 and provides standard contact lens features, including lens positioning and centration. In accordance with one exemplary embodiment, the outer zone 404 may include one or more stabilization mechanisms to reduce lens rotation when on eye.

In specific embodiments of the present invention, the mask may have an inner radius at any one of the at least one peripheral zones 408 and extend to the outer margin of the optic zone 402.

It is important to note that the various zones in FIG. 5 are illustrated as concentric circles, the zones may comprise any suitable round or non-round shapes such as an elliptical shape.

It is important to note that as the entrance pupil size of the eye and target vergence/accommodation varies among subpopulations. In certain exemplary embodiments, the lens design may be customized to achieve both good foveal vision correction and myopic treatment efficacy based on the patient's average pupil size. Moreover, as pupil size correlates with refraction and age for pediatric patients, in certain exemplary embodiments, the lens may be further optimized towards subgroups of the pediatric subpopulation with specific age and/or refraction based upon their pupil sizes. Essentially, the power profiles may be adjusted or tailored to pupil size to achieve an optimal balance between foveal vision correction, and increased depth of focus, and reduced IQ sensitivity.

Currently available contact lenses remain a cost effective means for vision correction. The thin plastic lenses fit over the cornea of the eye to correct vision defects, including myopia or nearsightedness, hyperopia or farsightedness, astigmatism, i.e. asphericity in the cornea, and presbyopia, i.e., the loss of the ability of the crystalline lens to accommodate. Contact lenses are available in a variety of forms and are made of a variety of materials to provide different functionality.

Daily wear soft contact lenses are typically made from soft polymer materials combined with water for oxygen permeability. Daily wear soft contact lenses may be daily disposable or extended wear disposable. Daily disposable contact lenses are usually worn for a single day and then thrown away, while extended wear disposable contact lenses are usually worn for a period of up to thirty days. Colored soft contact lenses use different materials to provide different functionality. For example, a visibility tint contact lens uses a light tint to aid the wearer in locating a dropped contact lens, enhancement tint contact lenses have a translucent tint that is meant to enhance one's natural eye color, the color tint contact lens comprises a darker, opaque tint meant to change one's eye color, and the light filtering tint contact lens functions to enhance certain colors while muting others. Rigid gas permeable hard contact lenses are made from siloxane-containing polymers but are more rigid than soft contact lenses and thus hold their shape and are more durable. Bifocal contact lenses are designed specifically for patients with presbyopia and are available in both soft and rigid varieties. Toric contact lenses are designed specifically for patients with astigmatism and are also available in both soft and rigid varieties. Combination lenses combining different aspects of the above are also available, for example, hybrid contact lenses.

It is important to note that the mask lens design of the present invention may be incorporated into any number of different contact lenses formed from any number of materials. Specifically, the mask lens design of the present invention may be utilized in any of the contact lenses described herein, including, daily wear soft contact lenses, rigid gas permeable contact lenses, bifocal contact lenses, toric contact lenses and hybrid contact lenses. In addition, although the invention is described with respect to contact lenses, it is important to note that the concept of the present invention may be utilized in spectacle lenses, intraocular lenses, corneal inlays and onlays.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic lens for at least one of slowing, retarding or preventing myopia progression, the ophthalmic lens comprising:
   a first zone at the center of the ophthalmic lens; and
   at least one peripheral zone surrounding the center and having a dioptric power that is different than that at the center; and
   an opaque mask extending from the at least one peripheral zone, thereby providing a lens power profile having substantially equivalent foveal vision correction to a single vision lens, and having a depth of focus and reduced retinal image quality sensitivity that slows, retards, or prevents myopia progression, the opaque mask being described by $$P(r)=P_{SEG}(r)+24\times\mathrm{SQRT}(5)\times SA\times r^2/3.25^4-12\times\mathrm{SQRT}\times SA/3.25^2, r<r_{MASK} \quad (1)$$

wherein P represents the dioptric power (D);
r represents a radial distance from a geometric lens center;
SA represents an amount of spherical aberration; and
$P_{SEG}(r)$ represents a step function that has a number of zones with different magnitudes.

2. The ophthalmic lens according to claim 1, wherein the reduced retinal image quality sensitivity is in a range of 0.2 to 1.7 for accommodative states ranging from about 1D to about 5D.

3. The ophthalmic lens according to claim 1, wherein the reduced retinal image quality sensitivity is in a range of 0.2 to 0.5 for accommodative states ranging from about 1D to about 5D.

4. The ophthalmic lens according to claim 1, wherein the ophthalmic lens comprises a contact lens.

5. The ophthalmic lens according to claim 1, wherein the ophthalmic lens comprises a spectacle lens.

6. The ophthalmic lens according to claim 1, wherein the ophthalmic lens compromises an intraocular lens, a corneal inlay, or a corneal onlay.

7. The ophthalmic lens according to claim 1, wherein an inner radius of the mask begins at 2 mm to 3 mm from the center of the ophthalmic lens.

8. The ophthalmic lens according to claim 1, wherein the mask comprises a colored or black ring.

9. The ophthalmic lens according to claim 1, wherein the power profile is multizonal and the at least one peripheral zone comprises two or more stepped zones.

10. The ophthalmic lens according to claim 1, wherein the power profile is a continuous power profile and the at least one peripheral zone comprises a continuous transition between two or more zones having different dioptric powers.

11. The ophthalmic lens according to claim 1, further comprising one or more stabilization mechanisms.

12. The ophthalmic lens according to claim 1, wherein the power profile is adjustable based upon pupil size to achieve a balance between foveal vision correction and an effective depth of focus and reduced retinal image quality sensitivity for treating myopia progression.

13. An ophthalmic lens for at least one of slowing, retarding or preventing myopia progression, the ophthalmic lens comprising:
   a first zone at the center of the ophthalmic lens; and
   at least one peripheral zone surrounding the center and having a dioptric power that is different than that at the center; and
   an opaque mask extending from the at least one peripheral zone, thereby providing a lens power profile having substantially equivalent foveal vision correction to a single vision lens, and having a depth of focus and reduced retinal image quality sensitivity that slows, retards, or prevents myopia progression, the opaque mask being described by $$P(r)=P_{pCHIP}(r)+24\times\mathrm{SQRT}(5)\times SA\times r^2/3.25^4-12\times\mathrm{SQRT}\times SA/3.25^2, r<r_{MASK} \quad (1)$$

wherein P represents the dioptric power (D);
r represents a radial distance from a geometric lens center;
SA represents an amount of spherical aberration; and
$P_{pCHIP}(r)$ represents a Piecewise Cubic Hermite Interpolating Polynomial curve control by number of points.

* * * * *